United States Patent [19]

Haung et al.

[11] Patent Number: 5,612,083
[45] Date of Patent: Mar. 18, 1997

[54] FLEXIBLE RUBBER ARTICLE AND METHOD OF MAKING

[75] Inventors: Wu-Nan Haung, Greer; Niles R. Manwill, Belton; Adana Muschelewicz, Easley; Fung-Bor Chen, Greer, all of S.C.

[73] Assignee: Maxxim Medical, Inc., Sugar Land, Tex.

[21] Appl. No.: 445,231

[22] Filed: May 19, 1995

Related U.S. Application Data

[62] Division of Ser. No. 264,588, Jun. 23, 1994, Pat. No. 5,545,451, which is a continuation of Ser. No. 896,642, Jun. 10, 1992, abandoned.

[51] Int. Cl.$^6$ .................................................. B05D 1/18
[52] U.S. Cl. ................ 264/233; 427/299; 427/314; 427/372.2; 427/384; 427/385.5; 427/402; 427/407.1; 427/413; 427/133; 427/2.3; 264/255
[58] Field of Search .................. 427/430.1, 2, 3, 427/133, 299, 314, 372.2, 384, 385.5, 402, 407.1, 413; 2/159, 167, 168; 428/421, 423.1, 423.9, 493

[56] References Cited

U.S. PATENT DOCUMENTS

| | | | |
|---|---|---|---|
| 3,382,138 | 5/1968 | Barth | 428/423.9 |
| 3,852,826 | 12/1974 | Schindler | 2/168 |
| 4,027,060 | 5/1977 | Essemplare et al. | 428/212 |
| 4,100,309 | 7/1978 | Micklus et al. | 427/2 |
| 4,143,109 | 3/1979 | Stockum | 264/112 |
| 4,302,852 | 12/1981 | Joung | 2/167 |
| 4,304,008 | 12/1981 | Joung | 2/167 |
| 4,310,928 | 1/1982 | Joung | 2/161 |
| 4,393,119 | 7/1983 | Concannon | 428/413 |
| 4,482,577 | 11/1984 | Goldstein et al. | 427/2 |
| 4,499,154 | 2/1985 | James et al. | 428/494 |
| 4,540,407 | 9/1985 | Dunn | 604/292 |
| 4,548,844 | 10/1985 | Podell et al. | 2/168 |
| 4,575,476 | 3/1986 | Podell et al. | 428/494 |
| 4,809,365 | 3/1989 | Chen et al. | 2/168 |
| 4,990,357 | 2/1991 | Karakelle et al. | 427/2 |
| 5,019,096 | 5/1991 | Fox, Jr. et al. | 623/1 |
| 5,084,514 | 1/1992 | Szczechura | 525/123 |
| 5,089,205 | 2/1992 | Huang et al. | 264/255 |

FOREIGN PATENT DOCUMENTS

WO9007286 7/1990 WIPO.

OTHER PUBLICATIONS

Mobay Corporation, Materials Safety Data Sheet, D–762 (Sep. 21, 1987).
Union Carbide Chemicals and Plastics, Material Safety Data Sheet, Polyox (Nov. 5, 1991).
Polysciences, Inc. Material Safety Data Sheet, Cat. No. 04652 (Apr. 17, 1990).
McGee Industries, Material Safety Data Sheet, McLube 1829 (Oct. 1991).
Heese et al., Allergir and Irritant Reactions To Rubber Gloves . . . J. Ami Acad. Dermatol 1991; 25:pp. 831–839.
Special Report—The Surgical Glove Beck et al. Bio Med Instrument & Tech. 1992, 26, 3 pp. 225–240.
Ceynadier et al., Allergenicity Suppression . . . Gloves Allergy, 1991, 46, pp. 619–625.
Union Carbide Corporation, Industrial Chemicals Catalog, p. 1, (1991–93).
Rohm & Haas, Material Safety Data Sheet, Rhoplex HG–74A, (May, 24, 1989).
Rohm & Haas, Catalog Data Sheet, Rhoplex HG–74, (1986).

*Primary Examiner*—James J. Seidleck
*Assistant Examiner*—Michael A. Williamson
*Attorney, Agent, or Firm*—Veal & Associates

[57] ABSTRACT

A multi-layer flexible article includes a first layer of natural rubber, a second layer of natural rubber, polyurethane, poly(acrylamide-acrylic acid, sodium salt) and polyethylene oxide and a third layer of acrylic copolymer and fluorocarbon telomer resin. The article is preferably a glove formed by the method of dipping a hand shaped mold into baths containing aqueous emulsions of the components used to form the layers. Gloves manufactured according to the method are substantially wet-hand and dry-hand donnable as compared to powdered latex gloves of similar size. The finished gloved is water washed and wet autoclaved to substantially reduce the protein content from the natural rubber and substantially remove other water extractable allergenic moieties. The washing and autoclaving renders the glove substantially hypoallergenic as compared to gloves not so treated.

7 Claims, No Drawings

FLEXIBLE RUBBER ARTICLE AND METHOD OF MAKING

This application is a divisional application under 37 C.F.R. § 1.60 of prior application Ser. No. 08/264,588 filed on Jun. 23, 1994 now U.S. Pat. No. 5,545,451, which is a file wrapper continuation of Ser. No. 07/896,642 filed on Jun. 10, 1992, now abandoned.

FIELD OF INVENTION

This invention relates to flexible rubber articles and more particularly to rubber surgeon's gloves and the method of making same.

BACKGROUND OF THE INVENTION

Flexible surgeon's gloves have very demanding requirements. They should have strength to resist tearing and should be thin and flexible to allow touch sensitivity. Further, they should be easy to don with wet or dry hands, but not be slippery for handling instruments.

Traditionally, surgeon's gloves have been manufactured by dipping molds or forms shaped like hands into baths containing natural rubber latex emulsions to form a film of the desired thickness. The film is then cured and the glove is removed from the mold. There are numerous problems with the manufacture and use of natural rubber gloves, an important one of which is the step of removal from the mold form. Removal from the mold can be difficult because the cured latex tends to be tacky and may adhere to the mold. Further, plain natural rubber latex gloves adhere to themselves and tend to be very difficult for a surgeon to don. This is particularly true in actual use situations where a sterility protocol is followed with the surgeon having wet hands. Techniques for addressing these problems have developed over the years. Initially, mold-release powders were dusted onto the surface of the mold forms to facilitate the removal of the glove from the form. Since the gloves are generally turned inside out as they are stripped from the form, these powders then aided the subsequent donning of the glove by the surgeon.

A wide variety of powders including talc, lycopodium, calcium carbonate, starch and modified starches has been used. Problems were identified with granuloma formation in patients and attributed to powders, particularly talc and its use has long been abandoned. Powdered gloves are still widely accepted today with epichlorohydrin modified starches being used quite successfully as powders for gloves by carefully controlling the material used and the amounts present on each glove.

As an alternate to powder, there are many disclosures of coating or treatments of gloves to modify their surface properties. These surface modifications have enjoyed varying degrees of success, as high quality powdered gloves are still considered optimum in terms of strength, tactility and ease of donning and removal.

There are two general ways of achieving natural rubber latex gloves which do not require powder for donning, chemical treatment of the rubber surface and adding materials onto a natural rubber surface. Representative of the chemical treatment is halogenation. Halogenation renders a rubber surface slippery, but it is most effective in conjunction with dry hands and additionally, the treatment may weaken and embrittle the overall film. It may also adversely affect the shelf life of a sterile glove.

There are many disclosures relating to adding materials to a rubber surface to improve its slip characteristics with both wet and dry skin. Representative of the disclosures is U.S. Pat. No. 4,575,476 to Podell et al. Podell et al. teaches a dipped rubber article having a skin contacting surface layer formed of a hydrogel polymer, such as polyvinyl pyrrolidone, polyhydroxyethyl acrylate or methacrylate and copolymers of these with each other or with acrylic or methacrylic acid, or with 2-ethylhexyl acrylate or a ternary copolymer of 2-hydroxyethyl methacrylate, methacrylic acid and 2-ethylhexyl acrylate.

Gloves prepared according to the teaching of Podell et al. can be shown to have less mechanical strength and reduced resistance to accelerated aging after sterilization compared to conventional powdered latex gloves. Under conditions of mechanical stress, such as extreme elongation as could occur during donning, they may partially delaminate and lose particles from the hydrogel coating. Further, they tend to be some what thicker than many powdered latex gloves thereby adversely affecting tactile sensitivity.

SUMMARY OF THE INVENTION

A multi-layer flexible article includes a first layer formed from natural rubber. A second layer is formed from natural rubber, polyurethane, poly(acrylamide-acrylic acid, sodium salt) and polyethylene oxide. A third layer is formed of acrylic copolymer and fluorocarbon telomer resin.

The article preferably may be a multi-layer surgeon's glove formed by dipping a hand shaped mold form in a series of baths. The preferred gloves are wet hand and dry hand donnable without the need for powder, and have greater strength compared to existing gloves of similar thickness. The structure of the gloves substantially reduces the incidence of air pinhole defects in manufacture of the gloves when compared to natural rubber latex gloves of similar thickness.

A method for manufacturing multi-layer articles, preferably gloves, includes dipping a hand shaped mold form in a series of baths to form on the surface of the mold, a patient contacting first layer of natural rubber, a wearer contacting layer of acrylic copolymer and fluorocarbon telomer and, intermediate to the wearer and patient contacting layers, a layer including natural rubber, polyurethane, poly(acrylamide-acrylic acid, sodium salt) and polyethylene oxide. The layers are washed, dried and cured to form a unitary structure, then the structure is everted as it is removed from the mold as a finished glove. The glove preferably then has a coating of lubricant applied to the surface, preferably followed by water washing, wet autoclaving and drying.

DETAILED DESCRIPTION

In accordance with the present invention, a preferred embodiment is a surgeon's glove formed on the surface of a mold. The manufacture begins with a surface of a cleaned and coagulant treated mold form which is coated by dipping the mold in a bath containing a natural latex rubber emulsion.

The glove molds are individual for the right and left hands. The molds are made in a variety of sizes and shapes corresponding to the various hand sizes for which the gloves are intended. The molds are preferably made of ceramic, most preferably porcelain, bisque or glazed, but other materials such as stainless steel, glass, hard woods and plastic may also be used.

Suitable coagulants include, but are not limited to, calcium nitrate, calcium chloride, acetic acid, magnesium acetate, and the like. A bath with an aqueous solution of about 20 to 25%, preferably 22.5%, calcium chloride with about 0.1 to 0.2% octoxynol, preferably 0.15%, is preferred for coating the molds with coagulant.

When the mold is dipped in the latex bath, the latex forms a patient contacting film on the surface of the coagulant coated mold which serves as a substrate for subsequent layers. The thickness of the substrate film and the subsequently applied layers is generally governed by the solids content of the emulsions, the quantity of the coagulant deposited on the mold, the temperature of the mold and the residence time of the mold in the baths.

In a preferred embodiment, where the substrate is formed from natural rubber latex, the porcelain molds are cleaned in a bath with aqueous sodium hypochlorite of concentration about 2.5 to 5%, preferably 3.0%, then rinsed with 120° to 150° F., preferably 135° F., water and allowed to drain. The rinsed and drained molds are then dipped in the calcium chloride coagulant bath with a temperature preferably about 110° to 130° F., most preferably 120° F. The molds with the coagulant on their surface are dried at about 210° to 270° F. for about 8 to 10 minutes, preferably 250° F. for 8.5 minutes, then dipped into a bath containing an aqueous anionic natural rubber latex emulsion.

The latex bath has a total solids content preferably about 25 to 35%, most preferably 30%, a temperature of preferably about 75° to 90° F., most preferably 82° F., and a pH about 9.5 to 10.6, most preferably, 10.1. The mold remains in the bath preferably about 20 to 30 seconds, most preferably 25 seconds, and is then removed, and preferably a minimum of 25 seconds is allowed for the latex film to gel. This forms the substrate layer.

The mold with the substrate layer on its surface is now dipped into a second bath containing an aqueous emulsion of anionic natural rubber latex, polyurethane latex, poly(acrylamide-acrylic acid, sodium salt) and polyethylene oxide. The total solids content of the bath is preferably about 13 to 15%, most preferably 14%, at a temperature preferably about 75° to 90° F., most preferably 82°, and a pH preferably about 7 to 10, most preferably 9. The proportions in parts per hundred of the components of the bath are anionic natural rubber latex, preferably 16 to 18, most preferably 17, polyurethane latex, preferably 11 to 13, most preferably 12, poly(acrylamide-acrylic acid, sodium salt) (10% carboxylic), preferably 0.35 to 0.43, most preferably 0.39, polyethylene oxide, preferably 0.26 to 0.32, most preferably 0.29, and water, preferably 69 to 71, most preferably 70. The mold is in the bath preferably about 25 to 45 seconds, most preferably 36, is then removed from the bath and dried, preferably about 160° to 200° F., most preferably, 180° F., preferably about 160 to 180 seconds, most preferably 180 seconds. This forms the intermediate layer.

Following the formation of the intermediate layer over the substrate layer on the surface of the mold, the mold with the layers on its surface is spray washed, preferably about 10 to 20 minutes, most preferably 15 minutes, preferably with 120° to 150° F., most preferably 130° F., water, then air dried preferably about 1 to 3 minutes, most preferably 2.5 minutes, preferably about 200° F.

After drying, the washed and dried mold with the layers on its surface has a wearer contacting layer applied over the intermediate layer by dipping the mold into a third bath containing an aqueous emulsion of acrylic copolymer and fluorocarbon telomer resin. The bath has a total solids content preferably about 2 to 3%, most preferably 2.5%, and a composition in parts per hundred of acrylic copolymer preferably about 1.41 to 1.88, most preferably 1.65, fluorocarbon telomer resin preferably about 34 to 38, most preferably 36, and water, preferably about 60 to 65, most preferably 62.35. The bath has a pH preferably about 6.5 to 9, most preferably 7.3. After dipping, the mold remains in the bath preferably 25 to 45 seconds, most preferably 36 seconds, then is withdrawn. The mold with the layers on its surface is then dried and cured preferably about 40 to 50 minutes, most preferably 44 minutes, preferably about 215° to 235° F., most preferably 225° F. This drying and curing step causes the layers to form a unitary structure and completes the formation of a glove.

The gloves are then stripped from the molds by everting them, having the effect of placing the last formed wearer layer on the inside. Preferably, the gloves are further treated by tumbling with a lubricant, preferably lanolin alkoxy ether, lanolin oil alkoxy ether, fluorocarbon telomer, silicone and the like, most preferably polydimethylsiloxane, preferably about 12 to 18 minutes, most preferably 15 minutes, preferably at 140° to 160° F., most preferably 150° F. to apply a coating of the lubricant to the surface.

Following the silicone treatment, the gloves are preferably water washed and subjected to a wet autoclaving cycle, preferably for 12 to 18 minutes, most preferably 15 minutes, preferably with a peak temperature about 200° to 300° F., most preferably 250° F., then tumble dried preferably about 20 to 30 minutes about 140° to 160° F., most preferably 30 minutes and 150° F.

Natural rubber latex is known to have a protein component, which is believed to be responsible for some allergic reactions to articles formed from natural rubber. The water washing and wet autoclaving steps followed by drying produce a significant reduction in the protein component as well as substantially reducing any other water extractable allergenic moieties present compared to gloves not so treated and other commercial surgeon's gloves. The protein content was determined by the Bradford test, a widely used method for protein quantitation. There are many reports in the recent literature attributing allergic reactions, and, in some cases, anaphylaxis, to the proteins present in natural rubber latex. The instant invention's wet autoclaving step is believed to substantially remove and denature these proteins. A comparison using the Bradford test for protein level was made between gloves of the instant invention and known commercially available gloves intended for similar applications.

| Protein Content (ug/g of glove) | Glove |
| --- | --- |
| 5.7 | Instant Invention |
| 117.0 | Surgikos MicroTouch |
| 85.1 | Baxter Triflex |

The ability of a material to cause irritation has historically been measured by the degree of irritation to rabbit eyes. Recent efforts to reduce the use of animals for this type of testing has led to the development of in vitro bacteria based tests. A test which has shown good correlation to the in vivo rabbit eye test for irritation potential is the luminescent bacterial toxicity test, provided under the trade name of Microtox. As shown in the table, the effective concentration ($EC_{50}$) is the weight of glove material in milligrams per 1000 milliliters of extraction medium required to reduce the light output of luminescent bacteria by 50%. The larger the number, the less cytotoxic the material. A comparison using the Microtox test between gloves of the instant invention and gloves produced under U.S. Pat. No. 4,575,476 shows that the irritation potential of the instant invention is significantly less.

| Bioluminescence ($EC_{50}$) | Glove |
|---|---|
| 37,000 | Instant Invention |
| 2,568 | U.S. 4,575,476 |

Gloves manufactured according to the above described method are substantially wet hand and dry hand donnable when compared to powdered natural rubber latex gloves of equivalent thickness and design. The intermediate layer and the wearer contacting layer applied to a natural rubber substrate can be used to impart a wet-slip and a dry-slip property to articles other than gloves as desired. When the coating layers are coupled with the water washing and wet autoclaving process steps, the detectable protein level from the natural rubber may be substantially reduced. Further, the concentration of any other water extractable moieties having allergenic potential present in the article may be substantially reduced.

The use of rubber gloves in medical practice has taken on added importance with the concern about Human Immunodeficiency Virus (HIV). The strength of a glove is an important consideration to users. The instant invention of a multi-layer glove surprisingly provides a statistically significantly higher tensile strength and tear strength compared to gloves manufactured according to the U.S. Pat. No. 4,575,476. This improved strength is particularly surprising because the gloves of the instant invention are stronger even when their thickness is less than those produced under the U.S. Pat. No. 4,575,476, a widely accepted powder-free glove. A comparison of physical properties is presented below using 30 samples for the instant invention and 20 samples of gloves produced under U.S. Pat. No. 4,575,476. The test values and standard deviation for the values are shown.

| Comparison of Physical Properties (ASTM D3577-88, D412, D624) | | |
|---|---|---|
| | Instant Invention | US 4,575,476 |
| Tensile, PSI | 4301 (240) | 3730 (407) |
| Tear, PLI | 346 (44) | 257 (39) |
| % Elongation | 903 (42) | 898 (33) |
| Modulus at 500% Elongation, PSI | 548 (24) | 425 (43) |
| Thickness (Mils) | | |
| Finger | 8.2 | 10.9 |
| Palm | 8.7 | 9.7 |
| Cuff | 8.4 | 9.3 |

The property of high strength coupled with reduced thickness resulted in the glove being rated acceptable or better for tactile sensitivity by 91% of users in a controlled use multi-site study in comparison to other premium quality surgical gloves, both powdered and powder-free. The gloves manufactured according to the instant invention preferably have a patient contacting layer about 0.05 to 0.45 mm thick, more preferably 0.15 to 0.30 mm, an intermediate layer about 0.005 to 0.20 mm thick, more preferably 0.013 to 0.05 mm and a wearer contacting layer about 0.0005 to 0.05 mm thick, more preferably 0.001 to 0.005 mm.

Another benefit of the instant invention is a reduced incidence of the "air pinhole" defect experienced in glove manufacture. In a well-run glove manufacturing operation, it is generally recognized that there is some running level of various defects. A defect level of about four per one thousand gloves has historically been seen for the "air pinhole" defect for natural rubber latex gloves. Most improvements to production processes are in the low percentage ranges. In the case of the instant invention, a substantial reduction of the "air pinhole" defect is achieved. In producing the instant invention a reduction in the occurrence of the "air pinhole" defect to below one in one thousand gloves may be achieved, thereby greatly increasing the yield for the process. It is believed that the application of the intermediate layer present in the instant multi-layer glove over the natural rubber substrate occludes many of the "air pinholes" present in the natural rubber layer, thereby reducing the occurrence of the "air pinhole" defect.

A preferred method for manufacture of gloves of the present invention is shown as an example. It should be recognized that the components and the parameters presented here are to be considered exemplary of the principles of the invention and are not intended to limit the invention to those components and parameters illustrated. The scope of the invention will be measured by the appended claims and their equivalents.

EXAMPLE

Gloves of the present invention were formed by executing the following steps:
1) Cleaned molds by dipping in an aqueous NaOCl (3.0%) bath, removed and rinsed with 135° F., water;
2) Applied coagulant to molds by dipping in an aqueous bath, removed and air dried (8.5 min., 250° F.)

| coagulant bath composition and conditions | |
|---|---|
| | Parts per hundred w/w |
| calcium chloride | 22.5 |
| (Triton X-100 Rohm and Haas) | 0.15 |
| water | 77.35 |
| temperature 120° F.; | |

3) Applied aqueous natural rubber latex to molds (substrate) by dipping in a bath for 30 seconds;

Latex Bath Composition and Conditions

Temperature 82° F.
pH 10.1
latex solids=30%;
4) Removed from latex bath and allowed to gel for 30 seconds;
5) Applied intermediate layer over substrate by dipping molds in intermediate bath for 36 seconds;

| intermediate bath composition and conditions | |
|---|---|
| | Parts per Hundred w/w |
| Natural rubber latex (56% solids) | 17.0 |
| Polyurethane latex (Impranil DLN; Mobay) | 12.0 |
| Polyethylene oxide | 0.29 |
| Water | 70 |
| Temperature | 82° F. |
| pH = 9 | |
| total solids = 14%; | |

6) Removed from intermediate bath and dried intermediate layer for 180 seconds at 200° F.;
7) Spray washed with water for 15 minutes at 130° F.;
8) Dried for 2.5 minutes at 200° F.;
9) Applied wearer side coating by dipping molds in wearer side bath for 35 seconds

| wearer side bath composition and conditions | |
|---|---|
| | Parts per hundred w/w |
| Acrylic copolymer (Rhoplex HG-74; Rohm and Haas, 42.5%) | 1.65 |
| Fluorocarbon telomer resin (McLube 1829; McGee Ind., 5%) | 36.0 |
| Water | 62.35 |
| Total solids | 2.5% |
| pH = 7.3 | |
| Temperature | 85° F.; |

10) Air dried and cured on molds; Time=44 minutes Temperature 225° F.;
11) Gloves were removed from mold by everting;
12) Gloves were tumbled with silicone lubricant (polydimethyl siloxane, G.E. SM-2140), 15 minutes at 150° F.;
13) Gloves were water washed (5 min. at 180° F.) and wet autoclaved for a 15 minute cycle with a peak temperature at 250° F.; and
14) Gloves were tumbled dry in 30 minutes at 150° F.

The gloves were subsequently sorted into pairs comprising a right hand and a left hand. A microorganism resistant package was formed from sealable paper laminate, and one pair of gloves was placed into each package. The package was then sealed and placed in a gamma radiation chamber for sterilization. Alternatively, packaging could be formed from non-woven, formed trays or the like, and sterilization could be conducted by steam, ethylene oxide or electron beam.

The process of applying a second layer and third layer, described above as intermediate and wearer contacting layers, has been shown to have utility in cases where the first layer is a material other than a film of natural rubber latex. Articles such as vinyl examination gloves formed from plastisol Polyvinylchloride (PVC) have shown benefits in powder-free donnability and in strength when coated with the intermediate and wearer contacting layers as described in the above example for natural rubber latex substrates. Additionally, the plastisol PVC gloves have also successfully been coated with just the wearer contacting layer directly by omitting the intermediate layer, thereby acquiring powder-free donnability. Other substrate films and flexible articles made from materials such as polyurethanes, polychloroprene, styrene/butadiene copolymer, nitrile latex and the like may benefit from the wet-slip and dry-slip properties imparted to articles by the application of the intermediate film followed by the wearer contacting coating. These articles could include other medical devices such as condoms, catheters and the like. Coatings of the wet-slip and dry-slip enhancing films followed by the above disclosed water washing and wet autoclaving process may also greatly reduce the reported incidences of anaphylaxis reported with natural rubber enema probes and the like based on the protein reduction and cytotoxicity testing reported above.

While a number of forms of the instant invention have been disclosed, it will be understood that the invention may be utilized in other forms and environments, so that the purpose of the appended claims is to cover all such forms of devices not disclosed but which embody the invention disclosed herein.

What is claimed is:

1. A process for making a flexible multilayered article comprising:

forming a first layer from an aqueous emulsion comprising natural rubber latex;

forming a second layer from an aqueous emulsion on said first layer comprising natural rubber latex, polyurethane, poly(acrylamide-acrylic acid, sodium salt) and polyethylene oxide; and forming a third layer from an aqueous emulsion on said second layer comprising acrylic copolymer and fluorocarbon telomer resin.

2. The process of claim 1 wherein said aqueous emulsion for forming said first layer is a bath having about 25 to 35% total solids content and a pH about 9 to 11 comprising an anionic emulsion of natural rubber latex.

3. The process of claim 1 wherein said aqueous emulsion for forming said second layer is a bath having about 10 to 20% total solids content and a pH about 7 to 10 comprising an anionic emulsion of natural rubber latex, an anionic emulsion of an aliphatic polyester polyurethane, poly(acrylamide/acrylic acid, sodium salt) and polyethylene oxide.

4. The process of claim 1 wherein said aqueous emulsion for forming said third layer is a bath having about 1.5 to 4% total solids content and a pH about 7 to 10 comprising an aqueous emulsion of acrylic copolymer and fluorocarbon telomer resin.

5. The process of claim 1 further including applying a lubricant coating selected from the group consisting of silicone, fluorocarbon telomer, lanolin oil alkoxy ethers and lanolin alkoxy ethers to at least one of a surface of said first layer and a surface of said third layer.

6. The process of claim 1 further including water washing and autoclaving said article.

7. The process of claim 6 wherein said water washing and autoclaving comprises a water wash for about 5 to 10 minutes at about 150° to 200° F. and a wet autoclaving cycle for about 10 to 20 minutes with a peak temperature about 180 to 280 degrees Fahrenheit which serves to substantially denature and extract proteins found in natural rubber latex and substantially remove water extractable allergenic moieties, thereby rendering said article substantially hypoallergenic compared to articles not so treated.

\* \* \* \* \*